United States Patent [19]

Mizukami et al.

[11] Patent Number: 5,705,750
[45] Date of Patent: Jan. 6, 1998

[54] ULTRASONIC SENSOR AND PIPETTING APPARATUS USING SAME

[75] Inventors: Kazuaki Mizukami; Masashi Yasuda; Hiroaki Arakawa, all of Hirakata; Mikio Hojo, Higashiosaka; Toshihiko Matsuhashi; Yoshio Ozawa, both of Hirakata; Atsushi Ogawa, Kyoto, all of Japan

[73] Assignee: Sanyo Electric Co., Ltd., Osaka, Japan

[21] Appl. No.: 617,951

[22] Filed: Mar. 13, 1996

[30] Foreign Application Priority Data

Mar. 15, 1995 [JP] Japan ................... 7-083210
Oct. 31, 1995 [JP] Japan ................... 7-308445
Oct. 31, 1995 [JP] Japan ................... 7-308446

[51] Int. Cl.$^6$ ................. G01N 29/00; B01L 3/02
[52] U.S. Cl. ............... 73/602; 73/64.53; 73/597; 73/620; 73/627; 73/864.24; 73/864.25; 222/420; 422/100; 422/68.1
[58] Field of Search ................ 73/64.53, 597, 73/599, 602, 620, 627, 629, 663, 579, 864.21, 864.23, 864.24, 864.25, 863.32; 364/561, 508, 509; 367/99, 127; 181/123, 124; 222/14, 59, 544, 566, 420; 422/100, 50, 68.1, 75; 604/295

[56] References Cited

U.S. PATENT DOCUMENTS

| | | | |
|---|---|---|---|
| 4,022,058 | 5/1977 | Brown | 73/194 A |
| 4,455,556 | 6/1984 | Koshio et al. | 342/47 |
| 4,480,485 | 11/1984 | Bradshaw et al. | 73/861.28 |
| 4,750,584 | 6/1988 | Tanaka et al. | 181/123 |
| 4,933,915 | 6/1990 | Bostrom | 367/99 |
| 5,206,838 | 4/1993 | Kashiwase | 367/99 |
| 5,428,997 | 7/1995 | Paulsen | 73/579 |
| 5,465,629 | 11/1995 | Waylett, Jr. | 73/864.24 |
| 5,557,047 | 9/1996 | Koide | 73/597 |

FOREIGN PATENT DOCUMENTS

WO 88/02124  3/1988  WIPO.
WO 93/25914  12/1993  WIPO.

*Primary Examiner*—Hezron E. Williams
*Assistant Examiner*—Richard A. Moller
*Attorney, Agent, or Firm*—Nikaido Marmelstein Murray and Oram LLP

[57] ABSTRACT

An ultrasonic sensor detects the time of rise of the first of transmitted waves and also detects peak points Po appearing in the waveform of received waves to detect a waveform reference point where the time-base coordinate of a phantom envelope connecting these peak points Po is a minimum. The time T2 of rise of the first of the received waves is calculated by adding a predetermined period of offset time To to the time t2 of the waveform reference point of the received waves to calculate the elapsed time ΔT from the time of rise of the first transmitted wave to the time of rise of the first received wave. The distance L to an object of measurement is calculated based on the result of calculation. The distance L to the object can be calculated alternatively based on the elapsed time ΔT' from a waveform reference point of the transmitted waves to the waveform reference point of the received waves. The sensor thus realized gives measurements with high accuracy even with use of ultrasonic waves of relatively low frequency.

22 Claims, 13 Drawing Sheets

ULTRASONIC SENSOR AND PIPETTING APPARATUS USING SAME

FILED OF THE INVENTION

The present invention relates to ultrasonic sensors for measuring distances and pipetting apparatus for pipetting or diluting reagents, samples and the like.

BACKGROUND OF THE INVENTION

With reference to FIG. 18, pipetting apparatus generally comprise a triaxially drivable table mechanism 18 controllable by a controller 19 and having a pipette head 15 attached to the output portion of the mechanism. Projecting downward from the head 15 is a pipette 16 for drawing in and discharging a reagent.

When the reagent is to be placed in small portions into cavities 21 in a plate 20 on a base 17, the pipette head 15 is moved by the operation of the table mechanism 18 to bring the lower end of the pipette 16 close to the cavity 21 in the plate 20, and the reagent is transferred from the pipette 16 into the cavity 21. When the reagent is to be added dropwise to other reagent 22 already placed in the cavity 21 for dilution or mixing, the reagent to be applied from the pipette 16 is brought into contact with the liquid surface of the reagent 22 in the cavity 21 to free the surface tension and thereby draw off the reagent from the pipette 16.

If the pipette 16 itself comes into contact with the reagent 22 in the cavity 21 at this time, the reagent adhering to the pipette 16 will be mixed with the other reagent in the subsequent pipetting step, so that the reagent needs to be drawn off from the pipette 16 with its lower end positioned slightly above the liquid surface of the reagent 22.

When the reagent is added for dilution or mixing, the pipette head 15 is lowered under the control of the controller 19 to bring the pipette 16 close to the liquid surface of the reagent 22 within the cavity 21 of the plate 20 to the greatest possible extent as stated above. However, since the liquid level of the reagent 22 differs from cavity to cavity, there arises a need to measure the liquid level every time to adjust the level of the pipette 16. The measurement of liquid level of the reagent 22 requires an accuracy of the order of 0.1 mm.

Although it is advantageous to use a laser measuring instrument from the viewpoint of the accuracy of distance measurements, the instrument is not usable for transparent reagents or reagents which are likely to undergo photochemical reaction since the reagent is irradiated with a laser beam in this case. Further because the liquid surface has irregularities due to surface tension, the direction of reflection is not definite, and the instrument has a problem with respect to sensitivity in receiving reflected light waves.

Accordingly, it is conventional practice to measure the distance to the liquid surface of the reagent 22 by an ultrasonic sensor 1 provided at one side of the pipette head 15 as seen in FIG. 18 and to feedback the measurement to the controller 19 for controlling the table mechanism 18.

The ultrasonic sensor 1 emits waves toward the object of measurement, receives the waves returning upon reflection at the object and measures the time from the emission of the waves and receiving of the reflected waves to determine the distance to the object based on the measurement.

Owing to the mechanical impedance of the transducer, the transmitted waves have such a waveform that the amplitude gradually increases first and thereafter gradually decreases as seen in FIG. 14. In corresponding relation with this waveform, the received waves are also similarly shaped. The received waves have the same frequency as the transmitted waves, and in peak value, a plurality of waves included in the received waves have a constant attenuation ratio to the corresponding waves included in the transmitted waves.

To be accurate, the time from the emission of the transmitted waves to the receiving of the received waves must be measured for the period from the rise of the first of the transmitted waves to the rise of the first of the received waves. To avoid an error in detecting the rise of the first of the received waves due to noise, the time when the amplitude of the waveform has exceeded a predetermined threshold level is taken as the time of rise of the first of the received waves as shown in FIG. 14.

As a result, the measurement obtained by the conventional ultrasonic sensor involves an error corresponding to several wavelengths of ultrasonic waves.

Furthermore, the size of received waves varies with variations in the distance to be measured and with the planarity of surface of the object, consequently altering the point of time when the threshold level is exceeded. Accordingly, the above-mentioned error differs for different sizes of received waves.

The error may be minimized by increasing the frequency of the transducer, but this results in marked attenuation of the amplitude during the propagation of ultrasonic waves and impaired measuring sensitivity.

SUMMARY OF THE INVENTION

An object of the present invention is to provide ultrasonic sensors adapted to give measurements with high accuracy even with use of ultrasonic waves of relatively low frequency, and pipetting apparatus equipped with the ultrasonic sensor.

The present invention provides a first ultrasonic sensor comprising first detecting means for detecting the time of rise of the first of transmitted waves, second detecting means for detecting a plurality of peak points appearing in the waveform of received waves and detecting a waveform reference point where the time-base coordinate is a minimum on a phantom envelope connecting the peak points, and calculating means for calculating the distance to an object of measurement based on the time of rise of the first of the transmitted waves detected by the first detecting means, the time of the waveform reference point of the received waves detected by the second detecting means and a predetermined period of offset time.

With the first ultrasonic sensor described, the time of rise of the first of the transmitted waves can be detected based on the time when supply of drive pulses to the transducer is started.

On the other hand, taken as the time Ps of rise of the first of the received waves is, as shown in FIG. 3, the time when a predetermined period of offset time To has elapsed from a waveform reference point Pb where the time-base coordinate is a minimum on a phantom envelope connecting a plurality of peak points Po appearing in the waveform of the received waves. Since any wave included in the waveform attenuates with the same attenuation ratio, phantom envelopes each connecting peak points Po extend through the same waveform reference point Pb in view of the geometric relation involved, regardless of the extent of attenuation as indicated in broken lines in FIG. 4.

Specifically stated, the period of time (offset time To) from the reference point Pb to the time Ps of rise of the first wave is constant regardless of the distance to the object of measurement. Accordingly, the offset time To can be predetermined by experiments as a value inherent in the sensor.

Stated more specifically, the waveform reference point is a zero cross point Pz where the phantom envelope intersects the zero level of the waveform as indicated in a broken line in FIG. 5.

In the case where the ground level of the waveform detecting signal is not deflected from the center of amplitude of the waveform in the specific construction described, the zero cross point Pz coincides with a point where the time-base coordinate is a minimum on the phantom envelope. Accordingly, the zero cross point Pz can be detected as the waveform reference point.

Specifically stated, the second detecting means comprises sampling means for sampling the received waves at 2n times (a is an integer of at least 1) the frequency of the transmitted waves, extraction means for extracting a plurality of apparent peak points regarded as peaks from the received wave sampled points obtained by the sampling means, and detector means for detecting a waveform reference point where the time-base coordinate is a minimum on a phantom envelope connecting the plurality of apparent peak points of the received waves obtained by the extraction means.

In the specific construction described, the extraction means extracts the plurality of apparent peak points from the received wave sampled points obtained at a specified frequency, i.e., at 2n times (n is an integer of at least 1) the frequency of the transmitted waves. The received waves have the same frequency as the transmitted waves and have true peak points Po the cycle of which is constant as shown in FIGS. 6 and 7, so that even if the apparent peak points P deviate from the true peak points Po as illustrated, the deviations ΔS in the time-base direction are equal for all waves. In view of the geometric relation involved, therefore, the phantom envelope connecting the true peak points Po and the phantom envelope connecting the apparent peak points P extend through the same waveform reference point Pb.

For example, n is 1, and the extraction means extracts all the received wave sampled points as apparent peak points, and the detector means detects a waveform reference point where the time-base coordinate is a minimum on a phantom envelope connecting these sampled points.

In the specific construction described, the received waves are sampled at twice the frequency of the transmitted waves, so that if one of the sampled points coincides with the true peak point Po of one wave in FIG. 6, all the other sampled points will be the true peak points Po of the other waves. Further even if the sampled points deviate from the true peak points Po, the deviations in the time-base direction of all the sampled points are equal as previously stated. Accordingly, the waveform reference point can be determined from the phantom envelope connecting these sampled points, i.e., the apparent peak points P.

Alternatively, n is, for example, at least 2, the extraction means compares the sampled points of the received waves with one another and extracts a plurality of apparent peak points which are regarded as peaks, and the detector means detects a waveform reference point where the time-base coordinate is a minimum on a phantom envelope connecting these apparent peak points.

With the specific construction described, sampled points which are different in deviation with respect to the time-base direction will repeatedly occur with the cycle of the received waves as shown in FIG. 7, whereas if a plurality of apparent peak points P are extracted from these sampled points, the deviations ΔS of these apparent peak points P in the time-base direction are equal. Accordingly, the waveform reference point can be determined from a phantom envelope connecting these apparent peak points P.

The present invention provides a second ultrasonic sensor comprising detecting means for detecting a plurality of peaks appearing in each of the waveforms of transmitted waves and received waves and detecting a waveform reference point where the time-base coordinate is a minimum on a phantom envelope connecting the peak points of each waveform, first calculating means for calculating the elapsed time from the waveform reference point of the transmitted waves to the waveform reference point of the received waves, and second calculating means for calculating the distance to an object of measurement based on the time value calculated by the first calculating means.

With the second ultrasonic sensor described, the reference point of each of the waveforms of the transmitted waves and the received waves is detected, and the elapsed time from the waveform reference point of the transmitted waves to the waveform reference point of the received waves is taken as the elapsed time from the time of rise of the first of the transmitted waves to the time of rise of the first of the received waves. As shown in FIG. 8 in this case, the period (period of offset time To) from time t1 of the waveform reference point of the transmitted waves to time T1 of rise of the first transmitted wave is equal to the period (period of offset time To) from time t2 of the waveform reference point of the received waves to time T2 of rise of the first received wave, as will be apparent geometrically. Accordingly the elapsed time ΔT' from the waveform reference point of the transmitted waves to the waveform reference point of the received waves is in match with the elapsed time ΔT from the time of rise of the first of the transmitted waves to the time of rise of the first of the received waves.

Specifically stated, the detecting means comprises sampling means for sampling the transmitted waves and the received waves at 2n times (n is an integer of at least 1) the frequency of the transmitted waves, extraction means for extracting apparent peak points regarded as peaks respectively from the transmitted wave sampled points and the received wave sampled points obtained by the sampling means, first detector means for detecting a waveform reference point where the time-base coordinate is a minimum on a phantom envelope connecting the apparent peak points of the transmitted waves obtained by the extraction means, and second detector means for detecting a waveform reference point where the time-base coordinate is a minimum on a phantom envelope connecting the apparent peak points of the received waves obtained by the extraction means.

With the specific construction described, even if the apparent peak points deviate from true peak points, a phantom envelope connecting the true peak points and the phantom envelope connecting the apparent peak points extend through the same waveform reference point.

For example, n is 1, and the extraction means extracts all the sampled points of the transmitted waves and the received waves as apparent peak points, and the first detector means and the second detector means each detect a waveform reference point where the time-base coordinate is a minimum on a phantom envelope connecting the sampled points of the corresponding waves.

In the specific construction described, the transmitted waves and the received waves are sampled at twice the frequency of the transmitted waves, so that even if one of the sampled points coincides with the true peak point Po of one wave and also if the sampled point deviates from the true peak point Po as shown in FIG. 6, the waveform reference point can be determined by the phantom envelope connecting the sampled points, i.e., the apparent peak points P.

Alternatively, n is, for example, at least 2, the extraction means compares the sampled points of each of the waveforms of the transmitted waves and the received waves with one another to extract apparent peak points regarded as peaks, and the first detector means and the second detector means each detect a waveform reference point where the time-base coordinate is a minimum on a phantom envelope connecting the apparent peak points of the corresponding waves.

With the specific construction described, sampled points which are different in deviation from the corresponding true peak point Po will occur cyclically as seen in FIG. 7, but the apparent peak points P are equal in deviation ΔS with respect to the time-base direction. Accordingly, the phantom envelope connecting the apparent peak points P provides a waveform reference point of the corresponding waves.

With the first and second ultrasonic sensors described, the elapsed time ΔT from the time of rise of the transmitted wave to the time of rise of the received wave shown in FIG. 14 is indirectly calculated. This eliminates the measurement errors inevitably involved in the conventional system.

The present invention further provides a pipetting apparatus which comprises the first ultrasonic sensor or second ultrasonic sensor of the invention installed, as directed downward, at one side of a pipette head.

With this pipetting apparatus, the object of measurement by the ultrasonic sensor is the surface of a liquid placed in a cavity of a plate. The distance to the liquid surface is calculated based on the time taken for the ultrasonic wave to reciprocatingly travel the distance from the sensor to the surface.

The ultrasolic sensor of the invention realizes accuracy of measurement not dependent on the wavelength of ultrasonic waves or the size of received waves and employs a measuring system which is free from errors in principle, consequently giving highly accurate measurements with a high resolution even with use of ultrasonic waves of relatively low frequency.

With the pipetting apparatus using the ultrasonic sensor of the invention, the pipette head can be positioned in place with high accuracy by virtue of the highly accurate measurement afforded by the sensor.

DETAILED DESCRIPTION OF EMBODIMENTS

The present invention will be described in detail with reference to three embodiments and the drawings.

First Embodiment

Figure 1:
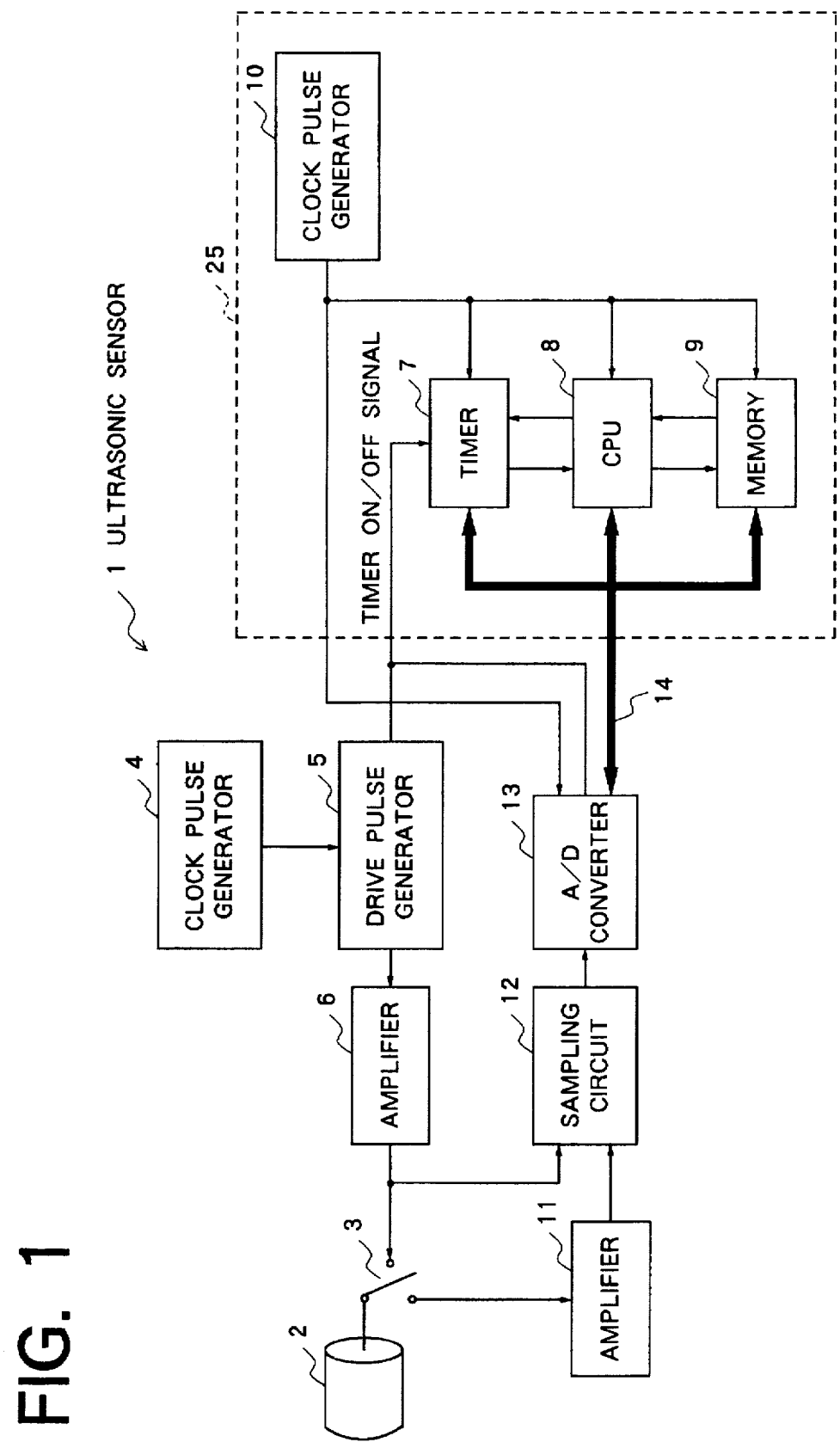
FIG. 1 is a block diagram showing the construction of an ultrasonic sensor embodying the invention.
Figure 2A:
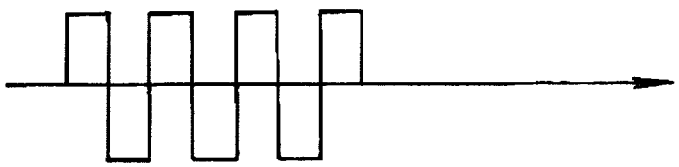
FIGS. 2(a) and 2(b) are waveform diagrams showing drive pulses and vibrations produced by a transducer, respectively.
Figure 2B:
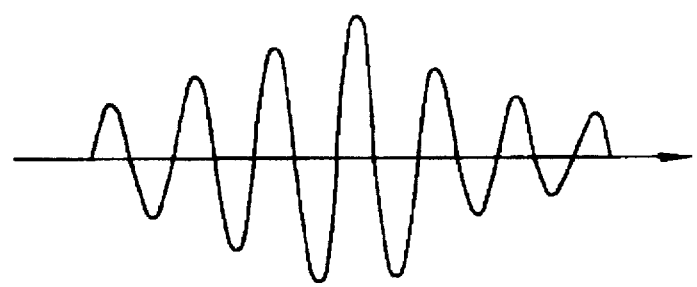

FIG. 1 shows this embodiment, i.e., an ultrasonic sensor 1, wherein the operating mode of a transducer 2 is changed over to a transmitting mode or to a receiving mode by a change-over switch 3. In the transmitting mode, a clock pulse generator 4 feeds clock pulses of 400 kHz to a drive pulse generator 5 to prepare drive pulses of 400 kHz. The drive pulses are amplified by an amplifier 6 and then supplied to the transducer 2 via the change-over switch 3. FIG. 2(a) shows these several drive pulses which have a constant peak value, whereas the vibration produced by the transducer 2 assumes such a waveform that the amplitude gradually increases first and thereafter gradually decreases as seen in FIG. 2(b) owing to the mechanical impedance of the transducer 2.

As shown in FIG. 1, the output of the amplifier 6 is fed also to a sampling circuit 12, and the signal thereby sampled is converted by an A/D converter 13 to digital data, which is fed to a microcomputer 25 by way of a bus line 14.

The microcomputer 25 has a timer 7, CPU 8 and memory 9 which operate based on reference clock pulses from a clock pulse generator 10. The timer 7 is initiated into operation by a timer ON/OFF signal input thereto from the drive pulse generator 5.

The data forwarded from the A/D converter 13 via the bus line 14 is processed by the CPU 8, whereby the time of rise of the first of transmitted waves is detected. The result is stored in the memory 9.

In the receiving mode, on the other hand, the transducer 2 shown in FIG. 1 detects received waves and feeds a detection signal to the sampling circuit 12 via an amplifier 11. The amplitude value of the waveform is sampled by the circuit 12 at a predetermined frequency (4 MHz). The result is converted by the A/D converter 13 into digital data, which is fed to the microcomputer 25. The microcomputer 25 stores the variations in the waveform as data of x-,y-coordinate system wherein the time t of sampling is taken as the x-coordinate, and the sampled amplitude value V as the y-coordinate.

To remove noise, a suitably threshold level is set for sampling the waveform of received waves, such that the data below the threshold level in the absolute value of amplitude is excluded.

Figure 3:
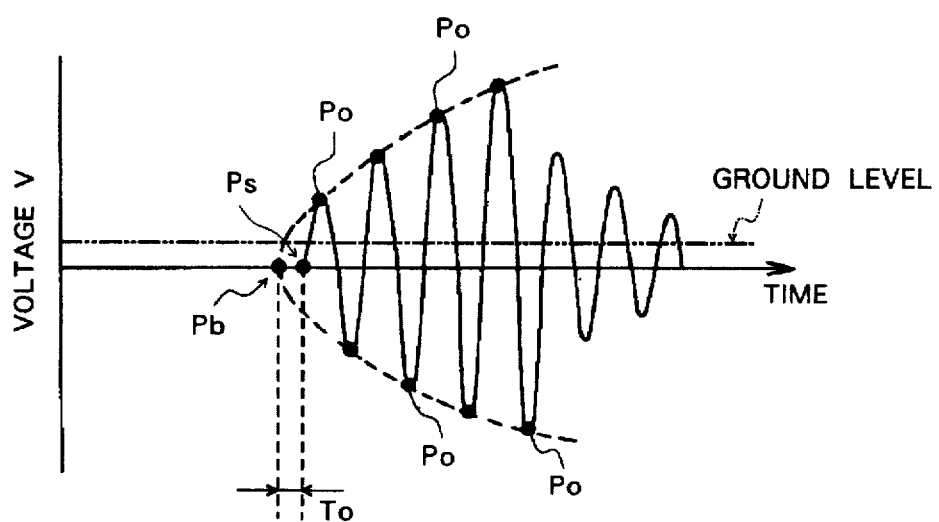
FIG. 3 is a diagram for illustrating a waveform reference point where the time-base coordinate is a minimum on a phantom envelope.
Figure 4:
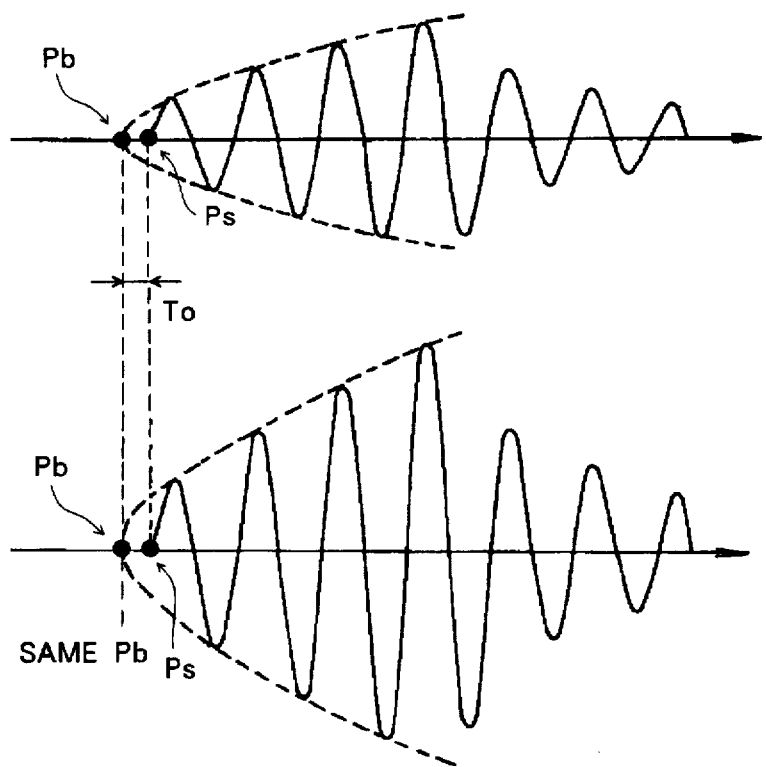
FIG. 4 is a diagram illustrating that the waveform reference point remains unchanged with variations in the attenuation ratio of the amplitude.

The microcomputer 25 thereafter detects a waveform reference point of the received waves to derive the time of rise the first of the received waves. When a phantom envelope connecting peak points Po appearing in the received waves is depicted as a quadratic curve as shown in FIG. 3, the waveform reference point Pb is the vertex of the curve where the time-base (-axis) coordinate of the curve is a minimum. Taken as the time Ps of rise of the first of the received waves is the time when a predetermined period of offset time To has elapsed from the waveform reference point Pb. Since any wave included in the waveform attenuates with the same attenuation ratio, phantom envelopes each connecting peak points extend through the same waveform reference point Pb in view of the geometic relation involved, regardless of the extent of attenuation as indicated in broken lines in FIG. 4. Stated more specifically, the period of time (offset time To) from the waveform reference point Pb to the time Ps of rise of the first wave is constant regardless of the distance to the object of measurement. Accordingly, the offset time To can be predetermined by experiments as a value inherent in the sensor.

The distance L to the object is then calculated based on the elapsed time from the time of rise of the first of the transmitted waves to the time of rise of the first of the received waves.

The distance L to the object thus calculated is output by a printer or shown on a display as desired.

Figure 9:
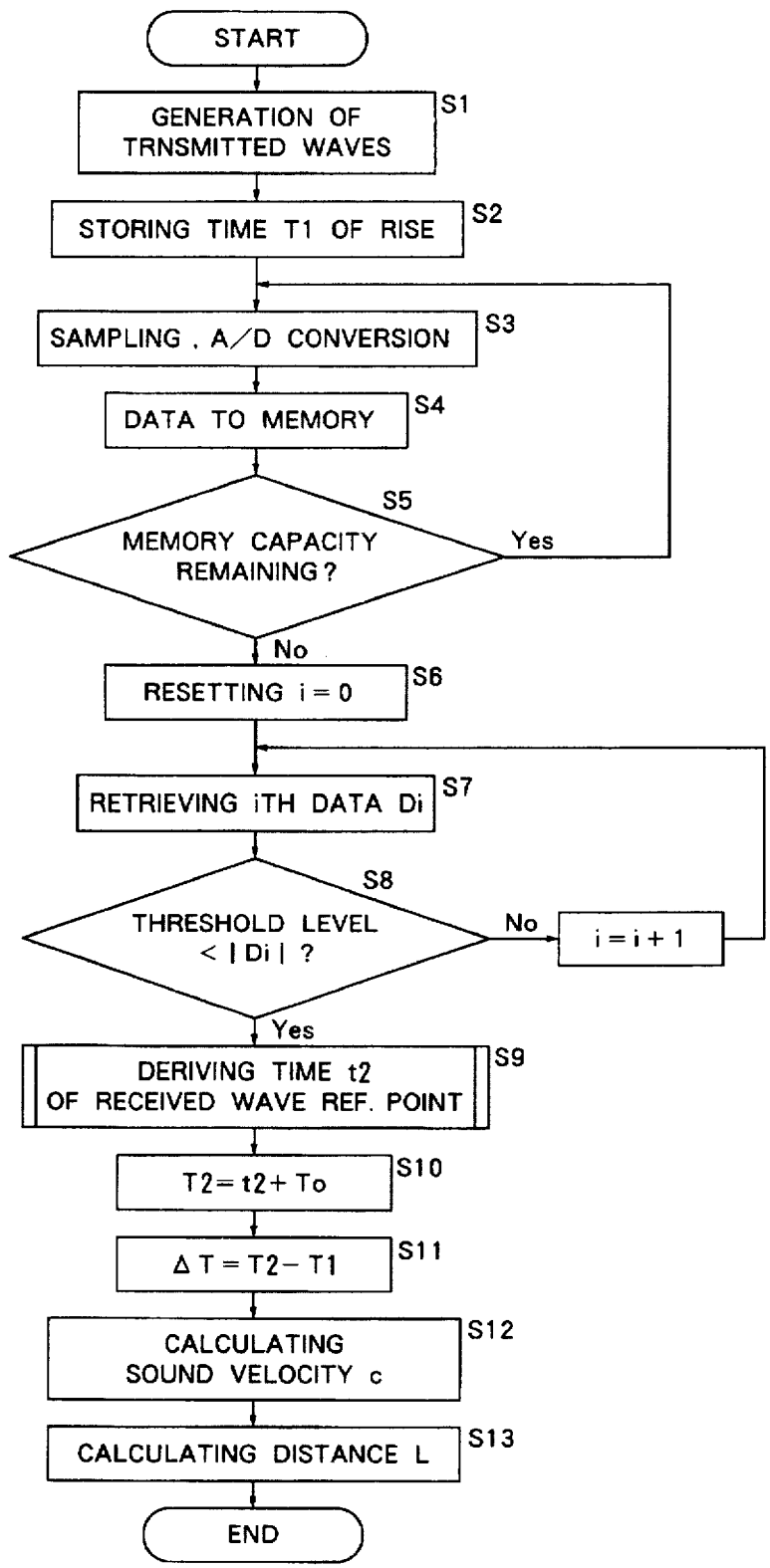
FIG. 9 is a flow chart showing a procedure for determining the distance to be measured.

FIG. 9 shows the procedure starting with the generation of transmitted waves and ending with the calculation of the distance L to the object of measurement.

In step S1, drive pulses are fed to the transducer 2 for the generation of transmitted waves, and in step S2, the time T1 of rise of the first transmitted wave is stored in the memory 9.

Step S3 subsequently performs sampling and A/D conversion of received waves, and the sampled data is stored in the memory 9 in step S4. An inquiry is made in step S5 as to whether any data storage area still remains in the memory 9. If the answer is affirmative, the sequence returns to step S3.

If the answer is negative, step S5 is followed by step S6 in which the counter variable i is reset (i=0).

In the next step S7, the ith data Di is retrieved from the memory 9. Step S8 inquires whether the absolute value of the data Di is greater than the threshold level. When the answer to the inquiry is "No," i is incremented, followed by step S7 again.

If the answer is affirmative, step S8 is followed by step S9, in which the time T2 of the waveform reference point of the received waves is derived. The procedure of step S9 will be described specifically later. In the next step S10, the time T2 of rise of the first of the received waves is calculated from Equation 1 below based on the time t2 of the received wave reference point and the predetermined offset time To.

$$T2 = t2 + To \qquad (1)$$

The offset time To, which is a value inherent in the ultrasonic sensor 1, can be a specified value predetermined experimentally, whereas it is desired to calculate the value To every time for more accurate distance measurement. The method of calculating the offset time will be described later in detail.

Subsequently in step S11, the elapsed time ΔT from the time T1 of rise of the first transmitted wave to the time T2 of rise of the first received wave is calculated from Equation 2 given below based on these times T1, T2.

$$\Delta T = T2 - T1 \qquad (2)$$

A sound velocity c is calculated from Equation 3 given below in step S13.

$$c = 0.607 \times tv + 331.5 \qquad (3)$$

wherein tv is the temperature of air detected by a temperature sensor at the time of measurement. Since the sound velocity is thus dependent on the temperature, it is necessary to measure the temperature and calculate the sound velocity every time the distance is to be measured so as to ensure high accuracy.

Finally in step S13, the distance L to the object of measurement is calculated from Equation 4 below, based on the elapsed time ΔT from the time of rise of the first transmitted wave to the time of rise of the first received wave and on the sound velocity c.

$$L = c \times \Delta T / 2 \qquad (4)$$

A detailed description will now be given of the procedure of the foregoing step S9, i.e., the procedure for deriving the waveform reference point of the received waves.

Figure 10:
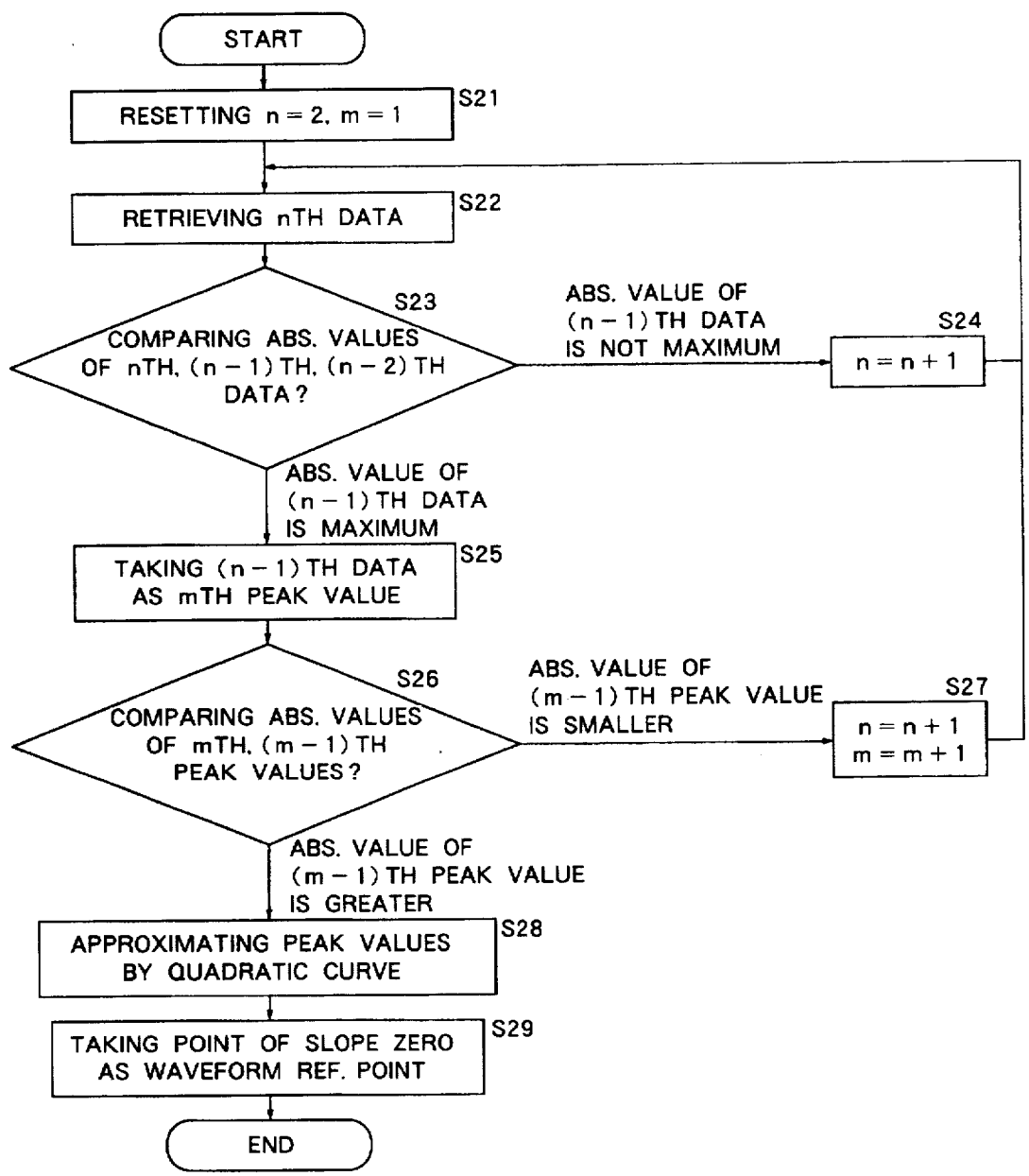
FIG. 10 is a flow chart showing a procedure for determining the waveform reference point.

With reference to FIG. 10, the required counter variables n and m are reset in step S21 first, and the nth data item is retrieved from the memory 9 in step S22.

In the next step S23, the absolute values of the nth, (n−1)th and (n−2)th data items are compared with one another, and if the absolute value of the (n−1)th is not a maximum, step S24 follows to increment n, whereupon the sequence returns to step S23.

When the absolute value of the (n−1)th data item is found to be a maximum in step S23, step S25 follows, in which the (n−1)th data item is taken as the mth peak value.

Subsequently in step S26, the absolute value of the mth peak value is compared with that of the (m−1)th peak value. If the latter is smaller, step S27 follows to increment n and m. The sequence then returns to step S22.

When the absolute value of the (m−1)th peak value is found greater in step S26, step S28 follows, in which the method of least squares is applied to the data as to the peak points to approximate a phantom envelope connecting the peak points by a quadratic curve, $t = aV^2 + bV + c$ wherein the time t is a function and the amplitude value V is a variable.

In step S29 is then calculated a point where the time-base coordinate is a minimum on the phantom envelope, i.e., a point (t2, V2) where the slope of the quadratic curve is zero. This point can be determined as amplitude value V2 and time t2 satisfying Equation 5 below, and these values V2, t1 are given by Equations 6 and 7, respectively.

$$dt/dV=2aV+b=0 \qquad (5)$$

$$V2=-b/2a \qquad (6)$$

$$t2=aVo^2+bVo+c \qquad (7)$$

The point (t2, V2) thus obtained is the waveform reference point, and the time t2 of the received wave reference point is derived.

A detailed description will be given of the method of calculating the period of offset time.

The ultrasonic sensor 1 is positioned above a flat reference surface at a predetermined distance Ho therefrom. The distance can be determined using a reference scale. The sensor 1 in this state is caused to emit waves of specified frequency toward the reference surface, followed by the procedure of FIG. 9, step S1 through step S9 to measure the time T1 of rise of the first of the transmitted waves and the time t2 of the waveform reference point of received waves and derive the period of time Te from time T1 to time t2.

On the other hand, the time Tr taken for the transmitted wave to reciprocatingly travel the predetermined distance Ho is theoretically given by Equation 8.

$$Tr=Ho\times 2/c \qquad (8)$$

wherein c is the sound velocity, which is calculated from Equation 3 in the same manner as in FIG. 9, step S12.

Figure 8:
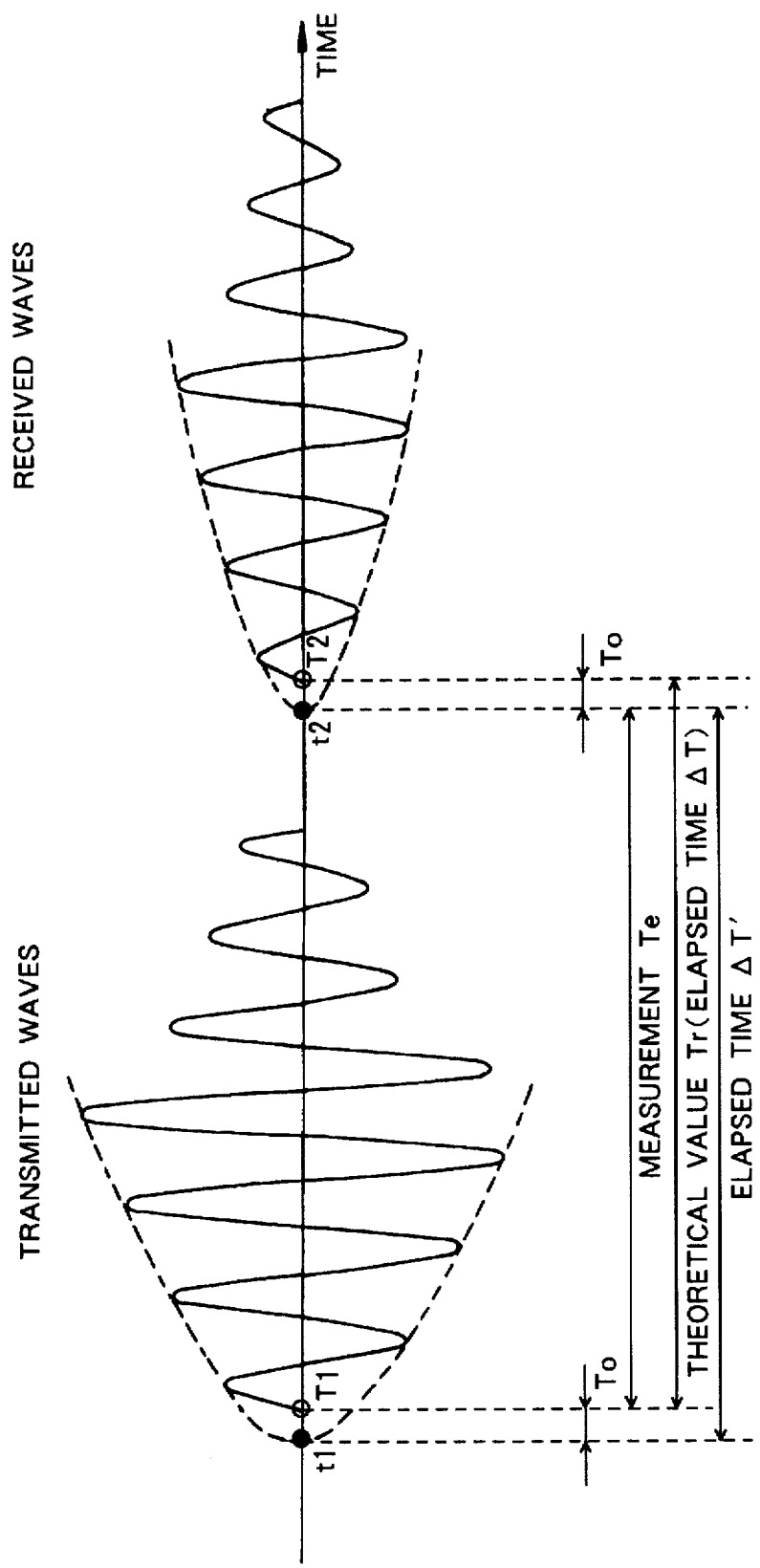
FIG. 8 is a diagram illustrating the principle of calculation of a period of offset time.

With reference to FIG. 8, the foregoing procedure determines the time Te from the time T1 of rise of the first transmitted wave to the time t2 of the waveform reference point of the received waves, and the theoretical calculation gives the time Tr from the time T1 of rise of the first transmitted wave to time T2 of rise of the first received wave. Accordingly, the period from the received wave reference point t2 to the time T2 of rise of the first received wave, i.e., the offset time To, can be given from Equation 9 below based on the measurement Te and the theoretical value Tr.

$$To=Tr-Te \qquad (9)$$

With the measuring procedure described above, the time T2 of rise of the receiving wave is calculated by adding the offset time To to the time t2 of the waveform reference point of the received waves in order to calculate the elapsed time ΔT from the time T1 of rise of the first transmitted wave to the time T2 of rise of the first received wave, whereas the same result is available by calculating the elapsed time ΔT' from the waveform reference point t1 of the received waves to the waveform reference point t2 of the transmitted waves.

In this case, the microcomputer 25 shown in FIG. 1 performs the same calculation procedure as in FIG. 10 for the sampled transmitted wave data supplied from the A/D converter 13 in the transmitting mode to detect the waveform reference point of the transmitted waves. The reference point is the vertex of a quadratic curve as representation of a phantom envelope connecting a plurality of peak points appearing in the transmitted waves, i.e., a point where the time-base coordinate of the curve is a minimum.

The distance L to the object of measurement is then calculated based on the elapsed time ΔT' from the waveform reference point of the transmitted waves to the waveform reference point of the received waves. As seen in FIG. 8, the offset time To of transmitted waves is equal to the offset time To of received waves as geometrically apparent, so that the elapsed time ΔT' from the transmitted wave reference point t1 to the received wave reference point t2 is in match with the elapsed time from the time T1 of rise of the transmitted wave to the time T2 of rise of the received wave.

Figure 11:
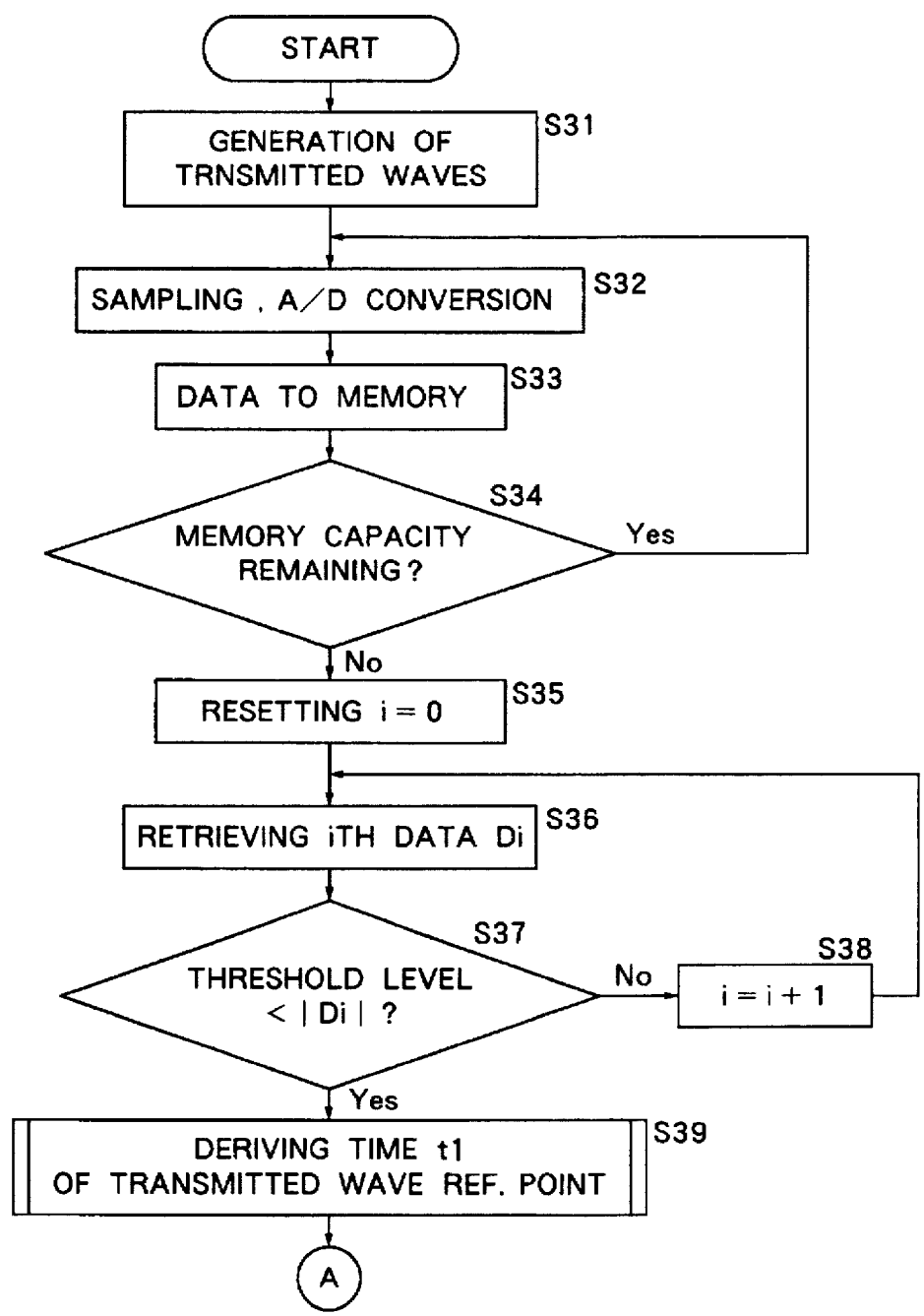
FIG. 11 is a flow chart showing the first half of another procedure for determining the distance to be measured.

Described below is the procedure to be followed in this case which starts with the generation of transmitted waves and ends with the calculation of the distance L to the object. With reference to FIG. 11, drive pulses are fed in step S31 to the transducer 2 for the generation of transmitted waves, followed by step S32 which samples the transmitted waves and received waves and effects A/D conversion.

Next, the sampled data is stored in the memory 9 in step S33. An inquiry is made in step S34 as to whether a data storage area remains in the memory 9. If the answer is affirmative, the sequence returns to step S32.

If the anwser is negative, step S34 is followed by step S35, in which the counter variable i is reset.

Subsequently in step S36, the ith data is retrieved from the memory 9. Step S37 inquires whether the absolute value of the data Di is greater than the threshold level. When the answer is negative, step S38 follows to increment count i, whereupon the sequence returns to step S36.

When the answer is found affirmative in step S37, step S39 follows to derive the time t1 of the waveform reference point of the transmitted waves. The reference point is derived by the procedure of FIG. 10.

Figure 12:
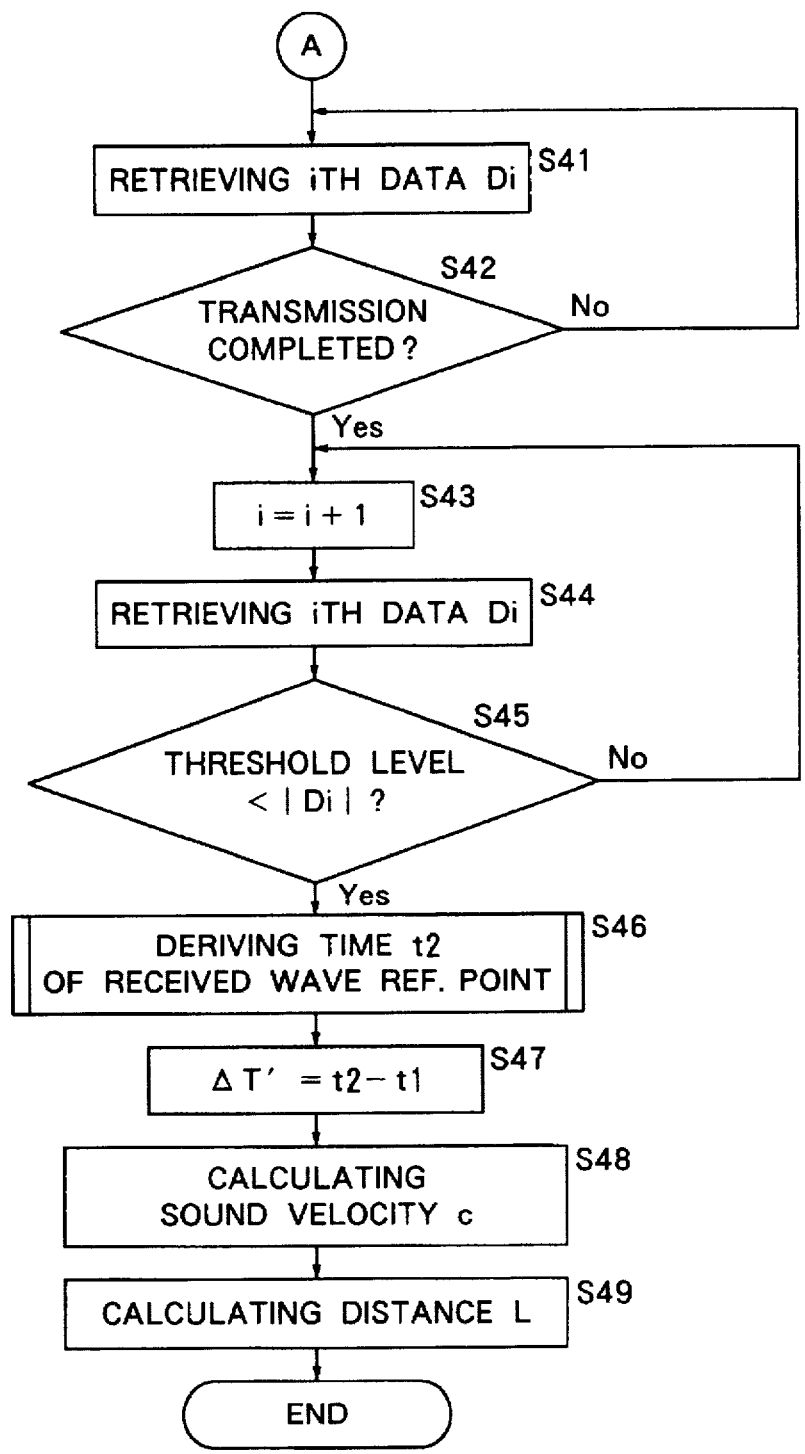
FIG. 12 is a flow chart showing the second half of the same procedure.

With reference to FIG. 12, the ith data Di is retrieved from the memory 9 in step S41, and step S42 inquires whether the emission of transmitted waves has been completed. If the answer to the inquiry of step S42 is negative, the sequence returns to step S41, whereas if the answer is affirmative, i is incremented in step S43.

The ith data Di is retrieved from the memory 9 in step S44, and an inquiry is made in step S45 as to whether the absolute value of the data Di is greater than the threshold level. When the answer is negative, step S45 is followed by step S43 again, while if it is affirmative, the sequence advances to step S46, in which the time t2 of the waveform reference point of received waves is derived. The reference point is derived by the procedure of FIG. 10.

In the following step S47, the elapsed time ΔT' from the waveform reference point of the transmitted waves to the waveform reference point of the received waves is calculated from Equation 10 below based on the times t1, t2 of the transmitted and received wave reference points.

$$\Delta T'=t2-t1 \qquad (10)$$

In the next step S48, the sound velocity c is calculated from Equation 3 in the same manner as in FIG. 9, step S12. Finally in step S49, the distance L to the object is calculated from Equation 11 given below, based on the elapsed time ΔT' from the transmitted wave reference point to the received wave reference point.

$$L=c\times \Delta T'/2 \qquad (11)$$

The ultrasonic sensor 1, according to the foregoing embodiment provides distance measurements with high accuracy and high sensitivity even with use of ultrasonic waves of relatively low frequency.

The waveform reference point is a point where the time-base coordinate is a minimum on the phantom envelope and is detectable independently of the voltage level, so that even if the ground level of the signal for detecting the waveform deviates from the center of amplitude of the waveform as indicated in a dot-and-dash line in FIG. 3, the detected position of the reference point remains unshifted free of any influence. Accordingly, the sensor provides measurements with high accuracy at all times and free from the error that would otherwise result from the deviation of the ground level.

When the offset time is calculated by the foregoing method every time a distance is to be measured, the measurement obtained can be of higher accuracy.

Figure 15:
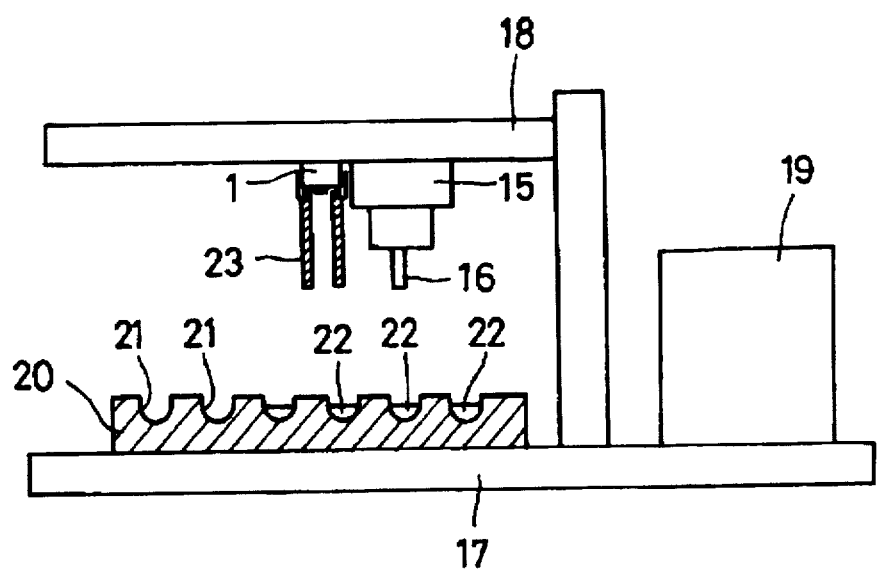
FIG. 15 is a front view partly broken away and showing a pipetting apparatus embodying the invention.

FIG. 15 shows a pipetting apparatus equipped with the ultrasonic sensor 1. Along with a pipette head 15, the sensor 1 is attached as directed downward to an output portion of a triaxially drivable table mechanism 18. The head and the sensor are always movable together by the operation of the table mechanism 18. A tube 23 of circular cross section is attached vertically to the wave emitting portion of the sensor 1. The tube 23 has the same inside diameter (about 7 mm) as cavities 21 in a plate 20. The length of the tube 23 is 60 mm.

When an agent is to be placed into the cavity 21 of the plate 20 on a base 17, the liquid level of other reagent 22 already placed in the cavity 21 is measured first by the ultrasonic sensor 1. In this case, the opening portion of the tube 23 is brought close to the opening portion of the cavity 21 of the plate 20 to the greatest possible extent to oppose the opening portions to each other in alignment as shown in FIG. 16.

When the sensor 1 emits ultrasonic waves in this state, the waves are guided by the inner peripheral surface of the tube 23 into the cavity 21 of the plate 20. Upon reflection at the liquid surface of the reagent 22, the waves are guided again by the inner peripheral surface of the tube 23 to return to the sensor 1.

Figure 19:
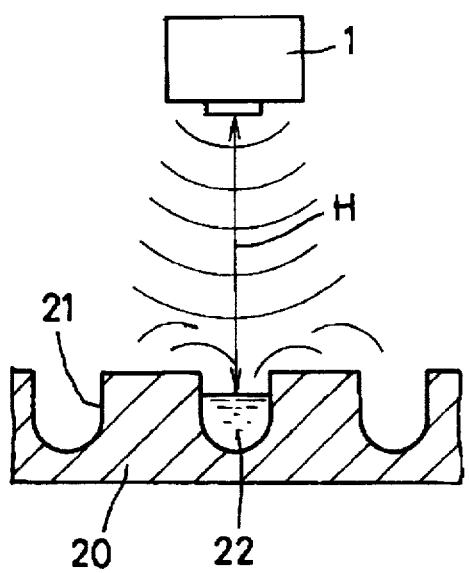
FIG. 19 is an enlarged fragmentary view in section corresponding to FIG. 16 and showing the conventional apparatus.

With the conventional pipetting apparatus wherein the ultrasonic sensor 1 is not provided with the tube 23, the ultrasonic waves emitted by the sensor 1 spead out as seen in FIG. 19. Some of the waves are projected onto the opening edge of the plate cavity 21, reflected from the edge and detected by the sensor 1. This entail the problem that an accurate measurement H is not available.

Figure 16:
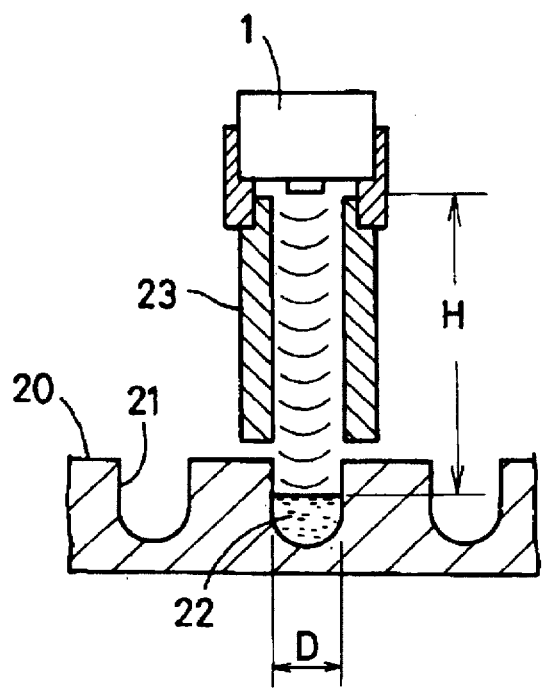
FIG. 16 is an enlarged fragmentary view in section showing the pipetting apparatus.

With the pipetting apparatus of the embodiment, on the other hand, the wave channel of the tube 23 has a cross sectional shape identical or substantially identical with the shape of opening of the plate cavity 21, and the distance is measured with the opening portion of the tube 23 positioned close to the cavity 21 of the to the greatest possible extent as seen in FIG. 16. This eliminates the likelihood that some of the waves emitted by the sensor 1 will be projected onto the opening edge of the cavity 21, permitting all the waves to be guided into the cavity 21 and reflected from the surface of the liquid in the cavity 21.

As a result, an accurate measurement H is obtained.

In calculating the period of offset time To, it is possible to utilize the tube 23 in place of the reference scale mentioned and a flat portion of the plate 20 as the reference surface.

Figure 17:
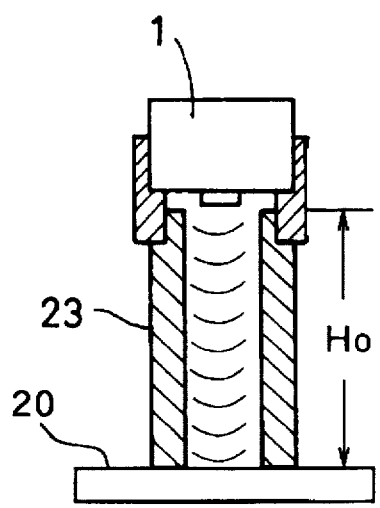
FIG. 17 is a diagram illustrating a method of calculating a period of offset time for use in the pipetting apparatus of the invention.
Figure 18:
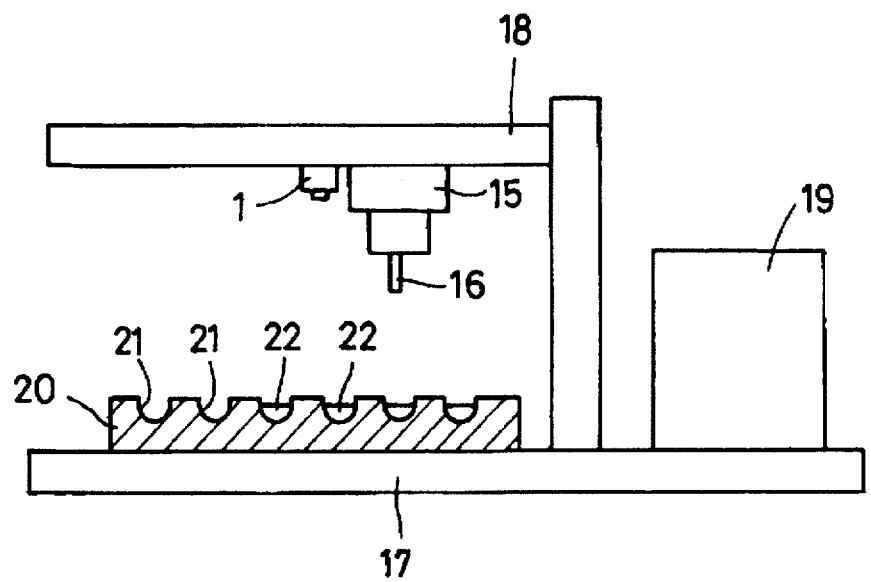
FIG. 18 is a front view partly broken away and showing a conventional pipetting apparatus.

Stated more specifically with reference to FIG. 17, the sensor 1 is caused to emit ultrasonic waves toward the flat portion of the plate 20 with the lower-end opening portion of the tube 23 in intimate contact with the flat portion. The distance Ho from the wave emitting portion of the sensor 1 to the flat portion is equal to the length of the tube 23, which is known (i.e., 60 mm in the present embodiment). It is therefore possible to theoretically determine the period Tr, shown in FIG. 8, from the time T1 of rise of the first transmitted wave to the time T1 of rise of the first received wave. The offset time To can be calculated by subtracting from the theoretical value Tr the measured value of the time, Te, from the time T1 of rise of the first transmitted wave to the time t2 of the received wave reference point. The reference scale is unnecessary since the sensor 1 is positioned in place in this way by using the tube 23.

The measurement obtained by the sensor 1 is fed to a controller 19 shown in FIG. 15 for use in controlling the position of the pipette head 15.

More specifically, the table mechanism 18 is operated based on the measurement provided by the sensor 1 to position the lower end face of the pipette 16 on the head 15 at a level 0.2 to 0.6 mm above the liquid surface of the reagent 22 in the plate cavity 21.

A plunger device (not shown) coupled to the pipette 16 is thereafter operated to discharge the reagent within the pipette 16. The reagent to be drawn off from the pipette 16 contacts in the form of a drop with the liquid surface of the reagent 22 in the plate cavity 21 and is freed from surface tension, whereby the reagent is placed into the cavity dropwise.

With the pipetting apparatus described, the liquid level is measured by the ultrasonic sensor 1 with high accuracy. This accurately positions the pipette head 15 when the reagent is to be drawn off, obviating the likelihood of the other reagent adhering to the end face of the pipette 16.

In the case where the inside diameter of the tube 23 is smaller than the inside diameter of the cavity 21, the reflection at the cavity opening edge is similarly precluded, whereas weak waves are then received by the sensor to result in an impaired S/N ratio. There arises a need for an expedient of improving the S/N ratio in this case.

Second Embodiment

The ultrasonic sensor 1 of the first embodiment is adapted to sample the amplitude value of transmitted waves and received waves at an optional constant frequency and to detect as a waveform reference point, the point where the time-base coordinate is a minimum on a phantom envelope connecting a plurality of peak points appearing in the received waves, whereas the ultrasonic sensor according to the present second embodiment is adapted to sample the amplitude value of waveform at 2n times (n is an integer of at least 1) the frequency of transmitted waves and to detect a waveform reference point where the time-base coordinate is a minimum on a phantom envelope connecting a plurality of apparent peak points appearing in the received waves In this case, the sampling circuit 12 of FIG. 1 samples the waveform amplitude value at 2n times (n is an integer of at least 1) the frequency of the transmitted waves in the transmitting mode and the receiving mode. In the receiving mode, the microcomputer 25 detects the waveform reference point of the received waves from the received wave sampled data supplied from the A/D converter 13 to derive the time of rise of the first received wave. When a phantom envelope connecting a plurality of apparent peak points P appearing in the received waves is depicted as a quadratic curve as shown in FIG. 3, the waveform reference point Pb is the vertex of the curve where the time-base coordinate of the curve is a minimum. Taken as the time Ps of rise of the first of the received waves is the time when a predetermined period of offset time To has elapsed from the waveform reference point Pb. Since any wave included in the waveform attenuates with the same attenuation ratio, the phantom envelope connecting the plurality of apparent peak points extends through the same waveform reference point Pb as a phantom envelope connecting true peak points in view of the geometric relation involved, so that the offset time To can be predetermined experimentally as a value inherent in the sensor.

Figure 6:
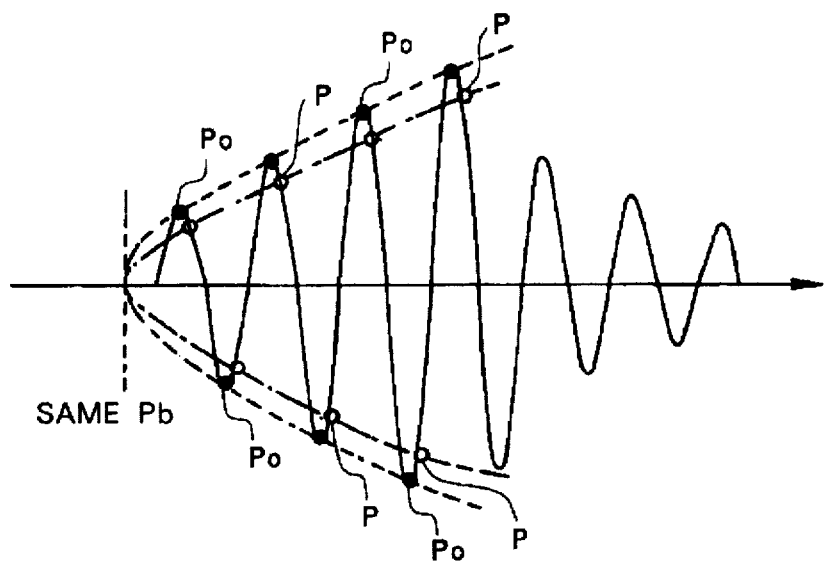
FIG. 6 is a diagram illustrating that the waveform reference point remains unchanged even when apparent peak points deviate from true peak points.
Figure 7:
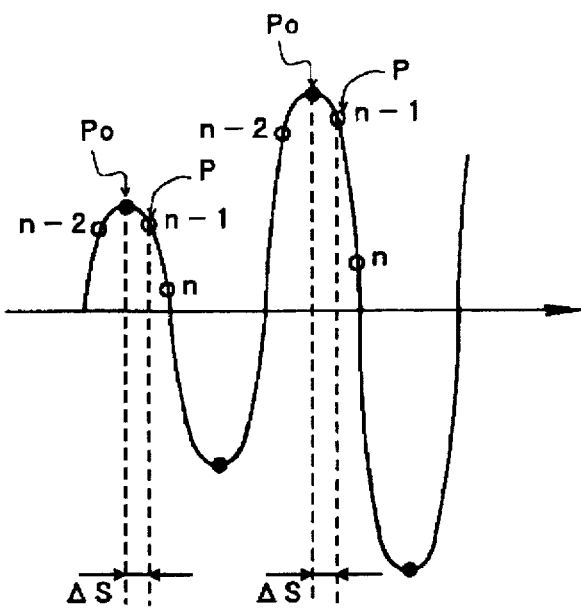
FIG. 7 is a diagram illustrating the relation between true peak points and sampled points.

The received waves have the same frequency as the transmitted waves and have true peak points Po the cycle of which is constant as shown in FIGS. 6 and 7. Therefore, even if the apparent peak points P deviate from the true peak points Po as illustrated, the deviations ΔS in the time-base direction are equal for all waves. In view of the geometric relation involved, accordingly, the phantom envelope connecting the true peak points Po and the phantom envelope connecting the apparent peak points P extend through the same waveform reference point.

In the case where the sampling frequency of the sampling circuit 12 is set at twice (n=1) the frequency of the transmitted waves, suppose one of the sampled points coincides with the true peak point Po of one wave as in FIG. 6. The other sampled points will then coincide respectively with the true peak points Po of all the other waves. Further even if the sampled points deviate from the true peak points Po, the deviations in the time-base direction of all the sampled points are the same. Accordingly, the waveform reference point can be determined by means of the phantom envelope connecting these sampled points, i.e., the apparent peak points P.

On the other hand, in the case where the sampling frequency of the sampling circuit 12 is set at 2n times (n≧2) the frequency of the transmitted waves, sampled points which are different in deviation with respect to the time-base direction will repeatedly occur with the cycle of the received waves as shown in FIG. 7, whereas if a plurality of apparent peak points P are extracted from these sampled points, the deviations ΔS of these apparent peak points P in the time-base direction are equal. Accordingly, the waveform reference point can be determined from a phantom envelope connecting these apparent peak points P.

The procedure starting with the generation of transmitted waves and ending with the calculation of the distance L to the object of measurement is basically the same as the procedure shown in FIG. 9 for the first embodiment, but step S3 performs sampling at 2n times (n≧1) the frequency of the transmitted waves and A/D conversion.

The time t2 of the Waveform reference point of the received waves is derived in step S9. The procedure for deriving the received wave reference point will be described in detail with reference to the case wherein the sampling frequency is twice the frequency of the transmitted waves.

Figure 13:
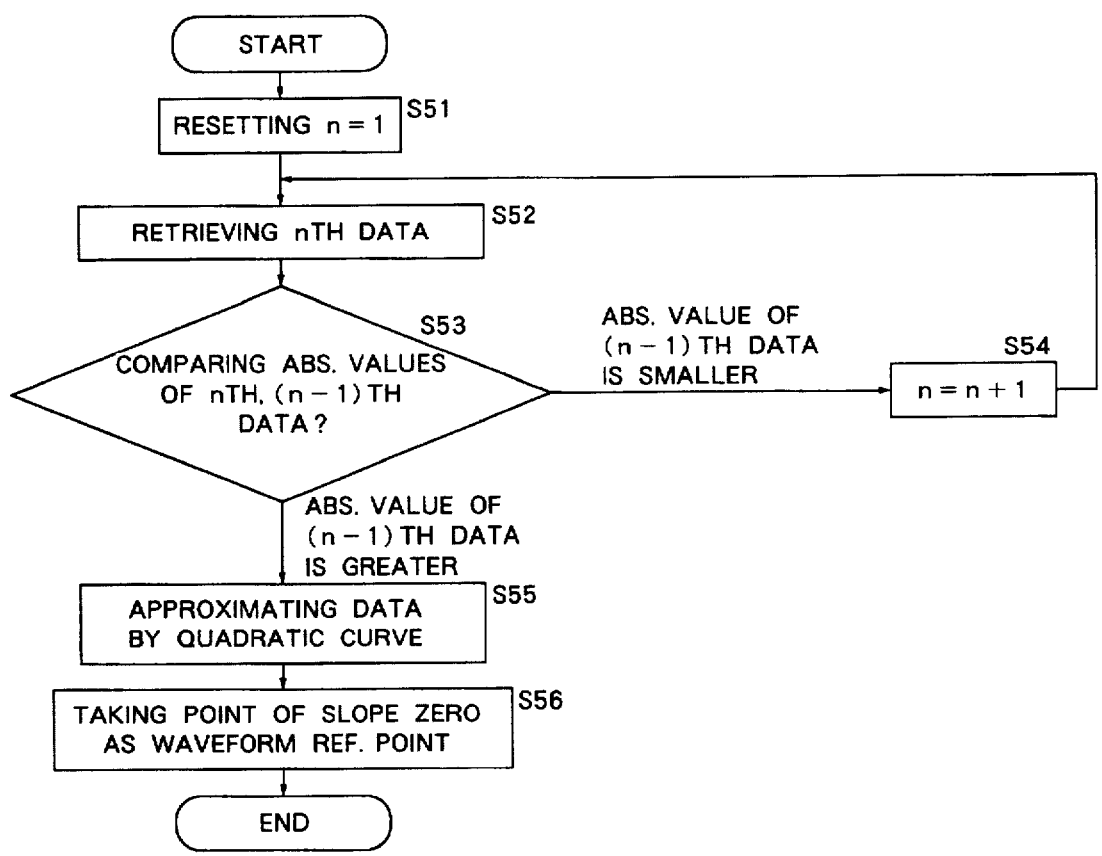
FIG. 13 is a flow chart showing a procedure for determining a waveform reference point in the case where the sampling frequency is twice the frequency of transmitted waves.
Figure 14:
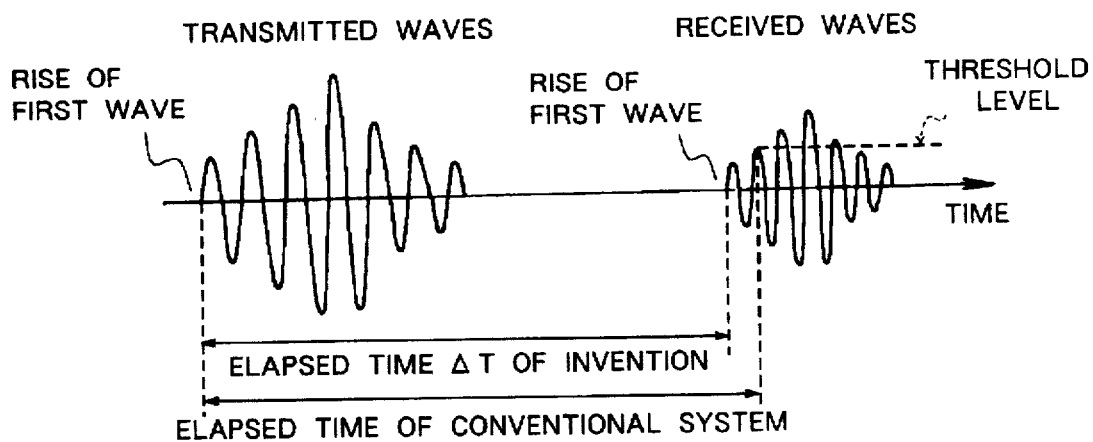
FIG. 14 is a diagram illustrating occurrence of a measuring error in the conventional system.

With reference to FIG. 13, the required counter variable n is reset first in step S51. In step S52, the nth data item is retrieved from the memory 9.

In the next step S53, the absolute value of the nth data item is compared with that of the (n−1)th data item, and if the (n−1)th data item is smaller, n is incremented, followed by step S52 again.

When the absolute value of the (n−1)th data item is found greater in step S53, step S55 follows, in which the method of least squares is applied to the data as to the sampled points to approximate a phantom envelope connecting the sampled points by a quadratic curve, t=aV²+bV+c wherein time t is a function, and amplitude value V is a variable.

In step S56 is then calculated a point where the time-base coordinate is a minimum on the phantom envelope, i.e., a point (t2, V2) where the slope of the quadratic curve is zero. This point can be determined as amplitude value V2 and time t2 satisfying Equation 5 previously given, and these values V2, t1 are given by the foregoing Equations 6 and 7, respectively.

The point (t2, V2) thus obtained is the waveform reference point, and the time t2 of the received wave reference point is derived.

In the case where the sampling frequency is the frequency of the transmitted waves multiplied by an even number of at least 4, the procedure to be performed is basically the same as is shown in FIG. 10 for the first embodiment. In this case, the (n−1)th sampled point is taken as the mth apparent peak point in step S25 of FIG. 10.

The time T2 of rise of the first received wave is then calculated by adding the period of offset time To to the time t2 of the waveform reference point of the received waves, and the distance L to the object of measurement is calculated based on the elapsed time ΔT from the time of rise of the first transmitted wave to the time of rise of the first received wave. The offset time To can be calculated by the method already described.

With the present embodiment as in the case of the first embodiment, the distance L to the object can be calculated also based on the elapsed time ΔT' from the waveform reference point of the transmitted waves to that of the received waves.

In the case of the ultrasonic sensor 1 of the present embodiment, the frequency at which the transmitted waves and received waves are sampled is related with the frequency of the transmitted waves, so that the waveform reference point can be derived even by sampling at a low frequency, for example, at two to 10 times the frequency of the transmitted waves.

Further the sensor 1 of the present embodiment, like the first embodiment, can be incorporated into a pipetting apparatus to achieve the same effect.

Third Embodiment

According to the first embodiment described, the waveform reference point is the vertex of a quadratic curve as representation of a phantom envelope connecting a plurality of peak points appearing in the received waves, i.e., the point where the time-base coordinate of the quadratic curve is a minimum, whereas with the ultrasonic sensor of the third embodiment, a phantom envelope connecting a plurality of peak points appearing in received waves is represented by a linear line, and the zero cross point where the line intersects the zero level of the waveform is taken as a waveform reference point.

Figure 5:
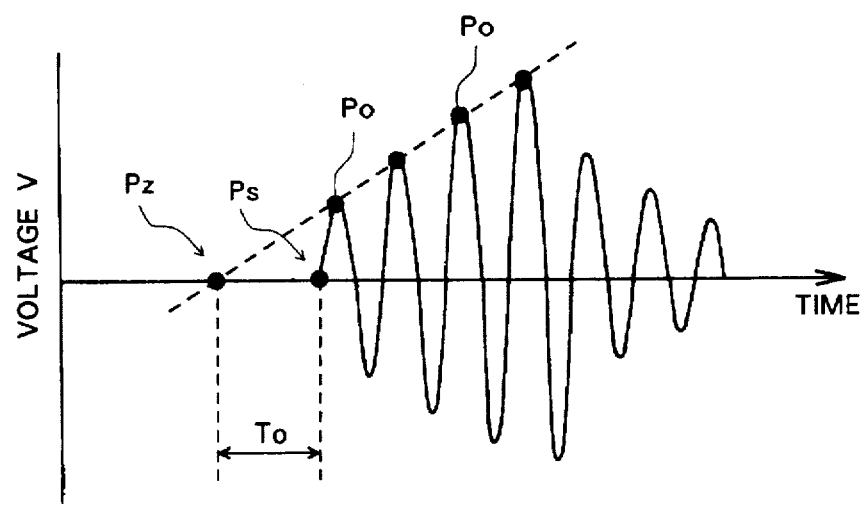
FIG. 5 is a diagram illustrating a zero cross point.

In the receiving mode in this case, the microcomputer 25 of FIG. 1 stores variations in the waveform in the memory 9 as data of two-dimensional coordinate system wherein the sampled time t is taken as the x-coordinate and the sampled amplitude value V as the y-coordinate. With the present embodiment, the data with negative y-coordinates is to be neglected. In the receiving mode, the microcomputer 25 further detects the waveform reference point of received waves to derive the time of rise of the first of the received waves. As seen in FIG. 5, an envelope connecting peak points Po appearing in the received waves is represented by a linear line. The waveform reference point Pz is then the zero cross point where the line intersects the zero level of the waveform, and the time when a predetermined period of offset time To has elapsed from the reference point Pz is taken as the time Ps of rise of the first of the received waves. Since any wave included in the waveform attenuates with the same ratio, the linear line extends through the same waveform reference point Pz regardless of the extent of attenuation, in view of the geometric relation involved. Thus, the period (offset time To) from the reference point Pz to the time Ps of rise of the first wave is constant regardless of the distance to the object of measurement. Accordingly, the offset time To can be predetermined experimentally as a value inherent in the sensor.

While the procedure starting with the generation of transmitted waves and ending with the calculation of the distance L to the object is basically the same as is shown in FIG. 9 for the first embodiment, only the sampled data which is positive in y-coordinate is stored in memory 9 in step S4.

The time t2 of the waveform reference point of the received waves is derived in step S9. The procedure for deriving the received wave reference point is basically the same as is shown in FIG. 10 for the first embodiment. The nth, (n−1)th and (n−2)th data items are compared with one another in step S23, and the mth peak value is compared with (m−1)th peak value in step S26.

The method of least squares is applied to the peak points in step S28 to approximate a phantom envelope connecting the peak points by a linear line, V=at+b wherein the amplitude value V is a function, and time t is a variable. The zero cross point (t2, 0) where V=0 is calculated in step S29. The zero cross point (t2, 0) provides a waveform reference point to derive the time t2 of the received wave reference point.

The time T2 of rise of the received wave is then calculated by adding the offset time To to the time t2 of the received wave reference point. The distance L to the object is calculated based on the elapsed time ΔT from the time of rise of the first transmitted wave to the time of rise of the first received wave. The offset time To can be calculated by the foregoing method.

With the present embodiment as is the case with the first embodiment, the distance L to the object can be calculated also based on the elapsed time ΔT' from the waveform reference point of the transmitted waves to that of the received waves.

The ultrasonic sensor 1 of the present embodiment is useful when the ground level of the signal for detecting the waveform is not deviated from the center of amplitude of the waveform.

Like the first embodiment, the sensor 1 of the present embodiment can be incorporated into a pipetting apparatus to achieve the same effect.

The description of the foregoing embodiments is intended to illustrate the present invention and should not be interpreted as limiting the invention defined in the appended claims or reducing the scope thereof. The sensors and apparatus of the invention are not limited to the foregoing embodiments in construction but can be modified variously without departing from the spirit of the invention as set forth in the claims.

For example, in calculating the elapsed time from the time of rise of the first transmitted wave to the time of rise of the first received wave, the embodiments described are adapted to calculate the time of rise of the first received wave by adding the offset time to the time of the waveform reference point of the received waves, whereas it is possible to calculate first the elapsed time from the time of rise of the first transmitted wave to the received wave reference point and add the offset time to the result of the calculation.

Although a quadratic curve is used to represent the phantom envelope according to the first and second embodiments, the envelope can be approximated by two intersecting straight lines. In this case, the intersection provides a waveform reference point.

Among the y-coordinates obtained by the measurement by the sensor 1, the positive data only is used according to the third embodiment, whereas the phantom envelope of transmitted or received waves can be obtained using the negative data in place of, or in addition to, the positive data. Furthermore, the phantom envelope can be approximated by a quadratic curve or exponential curve.

What is claimed is:

1. An ultrasonic sensor for measuring a distance to an object by transmitting waves to the object, receiving waves returning upon reflection at the object and measuring time from emission of the transmitted waves to receiving of the waves to determine a distance based on a resulting time measurement, the ultrasonic sensor comprising:

first detecting means for detecting time of rise of a first of the transmitted waves, second detecting means for detecting a plurality of peak points appearing in a waveform of the received waves and for detecting a waveform reference point as a vertex of a phantom envelope connecting the peak points, the vertex being a point where a time-base coordinate is a minimum on the phantom envelope, and calculating means for calculating the distance to the object based on the time of rise of the first of the transmitted waves detected by the first detecting means, a time of the waveform reference point of the received waves detected by the second detecting means and a predetermined period of offset time.

2. An ultrasonic sensor as defined in claim 1 wherein the waveform reference point is a zero cross point where the phantom envelope intersects the zero level of the waveform.

3. An ultrasonic sensor as defined in claim 1 wherein the second detecting means comprises:

sampling means for sampling the received waves at 2n times (n is an integer of at least 1) a frequency of the transmitted waves, extraction means for extracting a plurality of apparent peak points regarded as peaks from the received wave sampled points obtained by the sampling means, and detector means for detecting a waveform reference point as the vertex of the phantom envelope connecting the plurality of apparent peak points of the received waves obtained by the extraction means, the vertex being the point where the time-base coordinate is the minimum on the phantom envelop.

4. An ultrasonic sensor as defined in claim 3 wherein n is 1, the extraction means extracts all the received wave sampled points as apparent peak points, and the detector means detects the waveform reference point as the vertex of the phantom envelope connecting these sampled points, the vertex being the point where the time-base coordinate is the minimum on the phantom envelope.

5. An ultrasonic sensor as defined in claim 3 wherein n is at least 2, the extraction means compares the sampled points of the received waves with one another and extracts a plurality of apparent peak points regarded as peaks, and the detector means detects the waveform reference point as the vertex of the phantom envelope connecting these apparent peak points, the vertex being the point where the time-base coordinate is the minimum on the phantom envelope.

6. An ultrasonic sensor as defined in claim 1 which is provided with means for calculating the period of offset time by causing the ultrasonic sensor as installed above a flat reference surface at a predetermined distance therefrom to transmit waves of specified frequency to the reference surface, measuring the time of rise of the first of the transmitted waves and the time of a wave reference point of received waves, and calculating the time from the waveform reference point of the received waves to the time of rise of the first of the received waves based on the time measurements and a theoretical value of the time taken for the transmitted wave to reciprocatingly travel the predetermined distance to set the result of calculation as the offset time.

7. An ultrasonic sensor as defined in claim 1 wherein the object is the surface of a liquid placed in a cavity of a container.

8. An ultrasonic sensor for measuring a distance to an object by transmitting waves to the object, receiving waves returning upon reflection at the object and measuring time from emission of the transmitted waves to receiving of the waves to determine the distance based on a resulting time measurement, the ultrasonic sensor comprising:

detecting means for detecting a plurality of peaks appearing in each of waveforms of the transmitted waves and the received waves and for detecting a waveform reference point as a vertex of a phantom envelope connecting peak points of each waveform, the vertex being a point where a time-base coordinate is a minimum on the phantom envelop, first calculating means for calculating elapsed time from the waveform reference point of the transmitted waves to the waveform reference point of the received waves, and second calculating means for calculating the distance to the object based on a time value calculated by the first calculating means.

9. An ultrasonic sensor as defined in claim 8 wherein the waveform reference point is a zero cross point where the phantom envelope intersects the zero level of the waveform.

10. An ultrasonic sensor as defined in claim 8 wherein the detecting means comprises:

sampling means for sampling the transmitted waves and the received waves at 2n times (n is an integer of at least 1) a frequency of the transmitted waves, extraction means for extracting apparent peak points regarded as peaks respectively from the transmitted wave sampled points and the received wave sampled points obtained by the sampling means, first detector means for detecting the waveform reference point as the vertex of the phantom envelope connecting the apparent peak points of the transmitted waves obtained by the extraction means, the vertex being the point where the time-base coordinate is the minimum on the phantom envelope, and second detector means for detecting the waveform reference point as the vertex of the phantom envelope connecting the apparent peak points of the received waves obtained by the extraction means, the vertex being the point where the time-base coordinate is the minimum on the phantom envelope.

11. An ultrasonic sensor as defined in claim 10 wherein n is 1, the extraction means extracts all the sampled points of the transmitted waves and the received waves as apparent peak points, and the first detector means and the second detector means each detect the waveform reference point as the vertex of the phantom envelope connecting the sampled points of the corresponding waves, the vertex being the point where the time-base coordinate is the minimum on the phantom envelope.

12. An ultrasonic sensor as defined in claim 10 wherein n is at least 2, the extraction means compares the sampled points of each of the waveforms of the transmitted waves and the received waves with one another to extract apparent peak points regarded as peaks, and the first detector means and the second detector means each detect the waveform reference point as the vertex of the phantom envelope connecting the apparent peak points of the corresponding waves, the vertex being the point where the time-base coordinate is the minimum on the phantom envelope.

13. An ultrasonic sensor as defined in claim 8 wherein the object is the surface of a liquid placed in a cavity of a container.

14. A pipetting apparatus having a pipette head attached to an output portion of a head drive mechanism, a pipette directed downward and projecting from the pipette head for drawing in and discharging a liquid, and an ultrasonic sensor provided at one side of the pipette head and directed downward for measuring a distance to an object by transmitting waves to the object, receiving waves returning upon reflection at the object and measuring time from emission of the transmitted waves to receiving of the waves to determine the distance based on a resulting time measurement, the pipetting apparatus being characterized in that the ultrasonic sensor comprising:

first detecting means for detecting time of rise of a first of the transmitted waves, second detecting means for detecting a plurality of peak points appearing in a waveform of the received waves and for detecting a waveform reference point as a vertex of a phantom envelope connecting the peak points, the vertex being a point where a time-base coordinate is a minimum on the phantom envelope, and calculating means for calculating the distance to the object based on the time of rise of the first of the transmitted waves detected by the first detecting means, the time of the waveform reference point of the received waves detected by the second detecting means and a predetermined period of offset time.

15. A pipetting apparatus as defined in claim 14 wherein the waveform reference point is a zero cross point where the phantom envelope intersects the zero level of the waveform.

16. A pipetting apparatus as defined in claim 14 wherein the second detecting means comprises:

sampling means for sampling the received waves at 2n times (n is an integer of at least 1) a frequency of the transmitted waves, extraction means for extracting a plurality of apparent peak points regarded as peaks from the received wave sampled points obtained by the sampling means, and detector means for detecting the waveform reference point as the vertex of the phantom envelope connecting the plurality of apparent peak points of the received waves obtained by the extraction means, the vertex being the point where the time-base coordinate is the minimum on the phantom envelope.

17. A pipetting apparatus as defined in claim 14 wherein the object is the surface of a liquid placed in a cavity of a plate, and an ultrasonic wave emitting portion of the ultrasonic sensor has a tube attached thereto as directed downward and formed with a wave channel centrally thereof, the wave channel of the tube having a cross sectional shape identical of substantially identical with the shape of opening of the cavity.

18. A pipetting apparatus as defined in claim 14 wherein the object is the surface of a liquid placed in a cavity of a plate, and an ultrasonic wave emitting portion of the ultrasonic sensor has a tube attached thereto as directed downward and formed with a wave channel centrally thereof, the wave channel of the tube having a cross sectional shape identical or substantially identical with the shape of opening of the cavity, the ultrasonic sensor being provided with means for calculating the period of offset time by causing the sensor to transmit waves of specified frequency toward a flat portion of the plate with an opening portion of the tube in intimate contact with the flat portion, measuring the time of rise of the first of the transmitted waves and the time of a wave reference point of received waves, and calculating the time from the waveform reference point of the received waves to the time of rise of the first of the received waves based on the time measurements and a theoretical value of the time taken for the transmitted wave to reciprocating travel the wave channel to set the result of calculation as the offset time.

19. A pipetting apparatus having a pipette head attached to an output portion of a head drive mechanism, a pipette directed downward and projecting from the pipette head for drawing in and discharging a liquid, and an ultrasonic sensor provided at one side of the pipette head and directed downward for measuring a distance to an object by transmitting waves to the object, receiving waves returning upon reflection at the object and measuring time, from emission of the transmitted waves to receiving of the received waves to determine the distance based on a resulting time measurement, the pipetting apparatus being characterized in that the ultrasonic sensor comprising:

detecting means for detecting a plurality of peaks appearing in each of waveforms of the transmitted waves and the received waves and for detecting a waveform reference point as a vertex of a phantom envelope connecting the peak points of each waveform, the vertex being a point where a time-base coordinate is a minimum on the phantom envelope, first calculating means for calculating elapsed time from the waveform reference point of the transmitted waves to the waveform reference point of the received waves, and second calculating means for calculating the distance to the object based on a time value calculated by the first calculating means.

20. A pipetting apparatus as defined in claim 19 wherein the waveform reference point is a zero cross point where the phantom envelope intersects the zero level of the waveform.

21. A pipetting apparatus as defined in claim 19 wherein the detecting means comprises:

sampling means for sampling the transmitted waves and the received waves at 2n times (n is an integer of at least 1) a frequency of the transmitted waves, extraction means for extracting apparent peak points regarded as peaks respectively from the transmitted wave sampled points and the received wave sampled points obtained by the sampling means, first detector means for detecting the waveform reference point as the vertex of the phantom envelope connecting the apparent peak points of the transmitted waves obtained by the extraction means, the vertex being the point where the time-base coordinate is the minimum on the phantom envelope, and second detector means for detecting the waveform reference point as the vertex of the phantom envelope connecting the apparent peak points of the received waves obtained by the extraction means, the vertex being the point where the time-base coordinate is the minimum on the phantom envelope.

22. A pipetting apparatus as defined in claim 19 wherein the object is the surface of a liquid placed in a cavity of a plate, and an ultrasonic wave emitting portion of the ultrasonic sensor has a tube attached thereto as directed downward and formed with a wave channel centrally thereof, the wave channel of the tube having a cross sectional shape identical or substantially identical with the shape of opening of the cavity.

* * * * *